US00PP37426P2

(12) United States Plant Patent
Horvath

(10) Patent No.: US PP37,426 P2
(45) Date of Patent: May 12, 2026

(54) ***PANICUM VIRGATUM* PLANT NAMED 'Dust in the Wind'**

(50) Latin Name: *Panicum virgatum*
Varietal Denomination: Dust in the Wind

(71) Applicant: Brent Horvath, Fontana, WI (US)

(72) Inventor: Brent Horvath, Fontana, WI (US)

( * ) Notice: Subject to any disclaimer, the term of this patent is extended or adjusted under 35 U.S.C. 154(b) by 0 days.

(21) Appl. No.: 18/831,539

(22) Filed: Apr. 7, 2025

(51) Int. Cl.
*A01H 5/12* (2018.01)
*A01H 6/00* (2018.01)

(52) U.S. Cl.
USPC ..... Plt./384

(58) Field of Classification Search
USPC ..... Plt./384
See application file for complete search history.

(56) References Cited

PUBLICATIONS www.intrinsicperennialgardens.com/wp-content/uploads/Intrinsic-Intros-2024-v06a2-2.pdf.*

* cited by examiner

*Primary Examiner* — Susan Mccormick Ewoldt

(57) ABSTRACT

A new, *Panicum virgatum* plant as described and illustrated, characterized by an upright plant habit, a height of 137 cm, leaf color that starts at 146 B with tips colored 200 B throughout the season, and much of the fall foliage color maturing to 200 C on top of some 146 B.

1 Drawing Sheet

Figure 1:
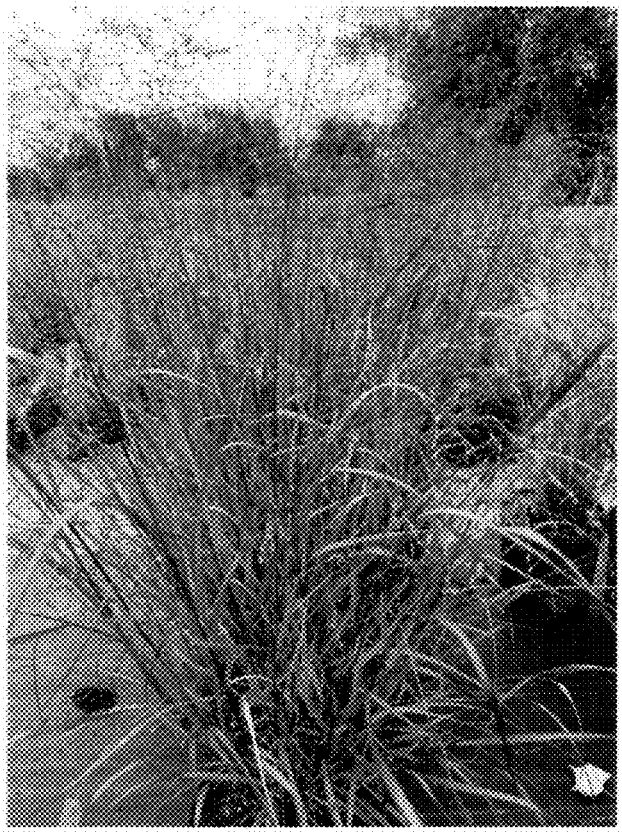

Latin name: *Panicum virgatum.*
Cultivar name: 'Dust in the Wind'.

BACKGROUND OF THE INVENTION

The present invention relates to a new form of *Panicum virgatum* plant named 'Dust in the Wind'. 'Dust in the Wind' is a seedling of *Panicum virgatum*, characterized by an upright plant with a height of 137 cm, and olive-green color foliage and purple fall color. The new plant was grown as a seedling from a mix of named and unnamed open pollinated *Panicum virgatum*, by the inventor at a wholesale perennial nursery in Hebron, IL USA in 2019. The selection of this plant was due to its upright stems, and clean olive-green colored foliage and purple fall color. Asexual, vegetative division propagation has been the only means of reproduction. Propagation has taken place at Hebron, IL since 2020. In 2022 we planted 300 plants in 1 gallon pots. To date these plants have remained uniform in height, and foliage color. The new *Panicum virgatum* has shown to be stable and identical in reproduction to the parent after making over 1000 vegetative divisions from 2020 to 2023. No plants of the new *Panicum virgatum* have been sold in this country, or anywhere in the world, prior to the filing of this application, nor has any disclosure of the new plant been made prior to the filing of this application with the exception of that which was disclosed by the inventor within one year of filing of this application and was derived directly from the inventor. The actual first date of sale is May 15, 2024.

SUMMARY OF THE INVENTION

In the following description, color references are made to The Royal Horticultural Society Colour Chart (copyright 2001). The new *Panicum virgatum* plant named 'Dust in the Wind' has shown the characteristics of upright plants with height of 137 cm, and clean olive-green colored foliage and purple fall color to be unique and stable. For purpose of the comparison the new plant will be referred to as 'Dust in the Wind'.

Plants of 'Dust in the Wind' can be compared to plants of *Panicum virgatum* 'Northwind', not patented. 1. 'Dust in the Wind' has a height of 137 cm compared to the height of *Panicum virgatum* 'Northwind' which has an average height of 180 cm. 2. 'Dust in the Wind' has a foliage color starting 146 B and becoming 146 B and 200 C compared to *Panicum virgatum* 'Northwind' which has foliage color of 137 A.

Plants of 'Dust in the Wind' can be also be compared to plants of *Panicum virgatum* 'Heavy Metal' not patented. 1. 'Dust in the Wind' has a height of 137 cm compared to the height of *Panicum virgatum* 'Heavy Metal' which has an average height of 120 cm. 2. 'Dust in the Wind' has a foliage color starting 146 B and becoming 146 B and 200 C compared to *Panicum virgatum* 'Heavy Metal' which has foliage color that is, blue-green. 'Dust in the Wind' has a more upright habit while the *Panicum virgatum* 'Heavy Metal' has an open habit. 3. 'Dust in the Wind' has a larger inflorescence to 37 cm long and 35 cm wide compared to *Panicum virgatum* 'Heavy Metal' which has an inflorescence that is 28 cm long and 25 cm wide.

DESCRIPTION OF PHOTOGRAPHS

FIG. 1. Shows potted plants blooming in August. Foliage color 146 B.

Figure 2:
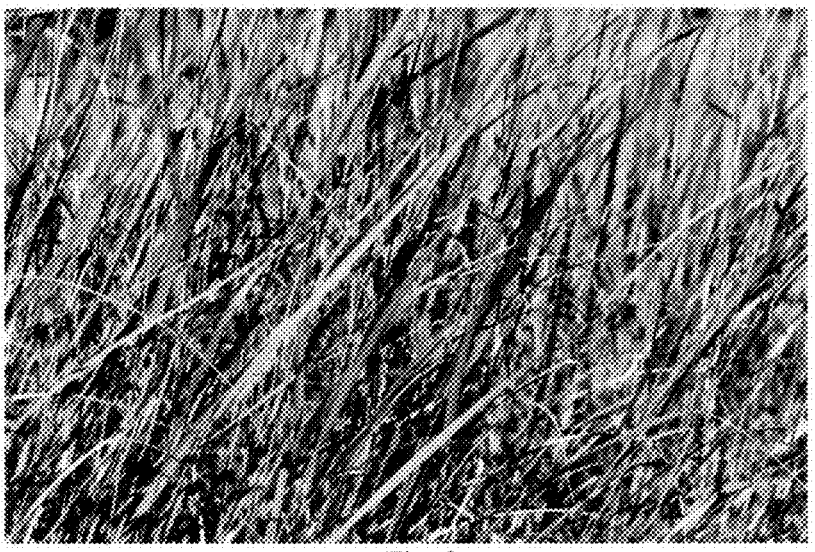

FIG. 2. Shows a mature plant in September with N187 B foliage color.

DETAILED BOTANICAL DESCRIPTION

In the following description, color references are made to The Royal Horticultural Society Colour Chart copyright 2001. The plant herein described is an established 2 year old plant growing in a garden, grown in full sun and irrigated in Hebron, IL USA. Measurements and numerical values represent averages of typical plants.

Botanical classification: *Panicum virgatum* cultivar 'Dust in the Wind'.

Parentage: Both male and female are *Panicum virgatum* unknown seedlings.

Propagation: Vegetative division.

Plant description: Overall habit of the new *Panicum virgatum* is clumping with upright culms topped by inflorescence with an overall color of 146 B with some parts turning N187 B beginning in August into September. Vigor is typical of other *Panicum*.

*Plant height*.—137 cm, Plant width: 85 cm.

Foliage and stems:

*Foliage description*.—Glabrous, flat blade, sheathed from node of attachment to ligule, linear.

*Type*.—Deciduous, grass growing in culms.

*Shape*.—Linear. Number of blades — typically 5 blades per stem.

*Sheath*.—4 mm wide flattened, 2-3 mm rolled up, 11 cm long, surface — glabrous.

*Ligules*.—Less than 1 mm long and — less than 1 mm wide.

*Blade*.—9 mm wide, up to 44 cm long.

*Adaxial leaf description*.—Leaf color starts at 146 B with tips colored 200 B throughout the season, much of the fall foliage color maturing to 200 C on top of some 146 B.

*Abaxial leaf description*.—Leaf color starts at 147 B with tips colored 200 B throughout the season, much of the fall foliage color maturing to 200 C on top of some 147 B.

Veins: Parallel, same color, 146 B, as surrounding leaf on top, midrib on the bottom of leaf is 1 mm wide and 146 C in color.

*Culm description*.—Erect, cylindrical, glabrous, two-thirds enclosed by leaf sheath, typically up to 5 leaves or nodes.

*Culm dimensions*.—3-4 mm wide, 95 cm long without the panicle, 137 cm including the panicle.

*Length of internodes*.—Average 15 cm. Color of the internodes is both 146 D and 183 B.

*Number of culms per clump*.—57 and 942 nodes per plant.

*Node description*.—Cylindrical. Number of nodes per culm — Average 6.

Flower inflorescence:

*Inflorescence type*.—Finely branched, terminal panicle, one panicle per culm, beginning in early August and remaining into winter.

*Panicle*.—Pyramidal, about 37 cm long and 35 cm wide, overall color 146 B with some parts N187 B.

*Rachis*.—Terete, branched, glabrous, glaucous 1-2 mm wide at the base and up to 37 cm long, branches 13 cm long and less than 1 mm diameter held at about a 40-70 degree angle above horizontal, color 146 B.

*Pedicel*.—Terete, 3-5 cm long and less than 1 mm diameter, color 146 B.

*Rachilla*.—6 mm long, and less than 1 mm in diameter, color 146 B.

*Spikelet*.—Usually has two flowers, both 1-2 mm wide and 3 cm long.

*Lower glume*.—1-2 mm wide, 3 mm long, color 146 B.

*Lemma*.—Outer and inner — both, 2 mm, 3 mm long, color 146 B.

*Flower number*.—Average 450 per culm.

*Gynoecium*.—Stigma — 2, color 146 B with N186 C.

*Androecium*.—Anthers — 2, color is N186 C. Pollen — color N186 C.

*Anther size*.—3 mm long by 1 mm wide, color N186 C.

*Fruit or seeds*.—Color is 199 B and 199 C, size is 2 mm wide, 3 mm long. Scent — no scent.

*Roots*.—Stiff, fibrous, and freely branching.

*Hardiness*.—United States Department of Agriculture Zones 4-9.

*Disease resistance*.—Plants are not more or less susceptible to any major pests or diseases.

I claim:

1. A new and distinct *Panicum virgatum* plant named 'Dust in the Wind' herein as described and illustrated, characterized by an upright plant habit, a height of 137 cm, leaf color that starts at 146 B with tips colored 200 B throughout the season, and much of the fall foliage color maturing to 200 C on top of some 146 B.

* * * * *